US00PP12445P2

(12) United States Plant Patent
Kaskel

(10) Patent No.: US PP12,445 P2
(45) Date of Patent: Mar. 12, 2002

(54) HEMEROCALLIS PLANT NAMED 'TIGER TIME'

(75) Inventor: Matthew Kaskel, Miami, FL (US)

(73) Assignee: Twyford Plant Laboratories, Inc., Sebring, FL (US)

( * ) Notice: Subject to any disclaimer, the term of this patent is extended or adjusted under 35 U.S.C. 154(b) by 0 days.

(21) Appl. No.: 09/563,341

(22) Filed: May 3, 2000

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Anne Marie Grünberg
(74) *Attorney, Agent, or Firm*—Foley & Lardner

(57) ABSTRACT

A new and distinct cultivar of Hemerocallis plant named 'Tiger Time' characterized by its abundant, showy, bright-orange flowers with red markings which are produced on tall-branched scapes. Plants of 'Tiger Time' bloom early and repeatedly throughout the growing season. Plants of 'Tiger Time' are evergreen and clump-forming, thus, they are attractive in landscapes. The plant grows vigorously and propagates easily by division or tissue culture.

2 Drawing Sheets

BACKGROUND OF THE INVENTION

The present invention comprises a new and distinct cultivar of Hemerocallis plant, hereinafter referred to by the cultivar name 'Tiger Time'. The genus Hemerocallis is a member of the family Liliaceae.

Hemerocallis comprises a genus of approximately 15 species of clump-forming, herbaceous perennials which are native to central Europe, China, and particularly, Japan. The flowers of Hemerocallis are lily-like and are borne in succession atop tall, frequently-branched scapes. Individual flowers last one day; thus, Hemerocallis is commonly know as 'Daylily' in commercial trade.

In recent years, Hemerocallis has been extensively hybridized, and many cultivars exist. Hemerocallis hybrids are hardy spring- and summer-blooming plants which are particularly well-adapted to landscape plantings.

The plants form clumps of fan-shaped crowns of vertically-ranked, keeled, strap-like leaves. Plants (individual crowns) range in size from approximately 20 cm to over 90 cm in spread. Depending upon the parentage, Hemerocallis hybrids may be deciduous, evergreen or semi-evergreen.

Hemerocallis hybrids come in a range of colors including orange, yellow, pink, reddish or purplish. The flowers are funnel-shaped or campanulate with six segments joined at the base into a tube.

Asexual propagation of Hemerocallis is frequently done by division. Propagation can also be done through the use of tissue culture practices.

The new cultivar 'Tiger Time' is a product of a planned breeding program and was originated by the inventor, Matthew Kaskel, from a cross made during such a program in Homestead, Fla. in April of 1990. The male and female parents are proprietary Hemerocallis selections designated by number codes which are maintained by the inventor and used for breeding purposes only. The selection comprising the new variety was chosen after commencement of flowering of the progeny in April of 1991.

Asexual reproduction of the new cultivar by tissue culture and division was performed by the inventor in Homestead, Fla. and has demonstrated that the combination of characteristics as herein disclosed for the new cultivar 'Tiger Time' are firmly fixed and are retained through successive generations of asexual reproduction.

BRIEF DESCRIPTION OF THE INVENTION

The following traits have been repeatedly observed and are determined to be basic characteristics of 'Tiger Time' which in combination distinguish this Hemerocallis as a new and distinct cultivar:

1. Flowers having three zones of color, which include bright orange with a dark eye zone and a yellow center;

2. Individual scapes are tall and branched with many buds which open in succession for approximately 4 weeks;

3. Spent flowers shrivel, become inconspicuous, drop from the scape quickly, and do not interfere with the opening of subsequent flowers;

4. Plants rebloom throughout a 90-day blooming season;

5. Plants grow vigorously and propagate rapidly by division and tissue culture; and 6. Plants have evergeen foliage and a clumping habit making them attractive in landscapes even when not in bloom.

'Tiger Time' has not been observed under all possible environmental conditions. The phenotype of the new cultivar may vary significantly with variations in environment such as temperature, light intensity, daylength and humidity, without any change in genotype.

BRIEF DESCRIPTION OF THE DRAWING

The accompanying color photographic illustrations show typical characteristics of Hemerocallis 'Tiger Time', with colors being as nearly true as possible with illustrations of this type.

The first drawing shows a 10-month-old plant of 'Tiger Time' grown from tissue culture and flowering in a landscape setting.

The second drawing is a close-up view showing the characteristics of the flowers and scape.

DETAILED BOTANICAL DESCRIPTION

The following observations, measurements and values describe plants grown in Sebring, Fla., under landscape conditions which closely approximate those generally used in horticultural practice. Color references are made to The Royal Horticultural Society (R.H.S.) Colour Chart, except where general color terms of ordinary significance are used.

Classification:

*Commercial*.—Hemerocallis cv. 'Tiger Time'.

Parentage:

*Male parent*.—Proprietary selection of Hemerocallis.

*Female parent*.—Proprietary selection of Hemerocallis.

Propagation: Vegetative, by tissue culture or division.

Plant:

*Form/growth habit*.—Clump-forming, fan-shaped crowns of vertically ranked, opposite, smooth, keeled, ligulate leaves.

*Height*.—Approximately 87 cm to 100 cm including inflorescence.

*Width*.—Approximately 90 cm to 120 cm.

Foliage:

*Size*.—Mature leaves are approximately 70 cm to 85 cm long and 3.0 cm to 3.5 cm wide (flattened).

*Shape*.—The leaf blade is ligulate with an acute tip. The margins are entire. The leaves are curved over their length. The leaf is keeled with the tip slightly twisted and curved downward.

*Surface texture*.—The leaf blade is relatively thin with a smooth surface.

*Color*.—Upper and lower surfaces are dark-green, RHS 137B–C.

*Average number*.—Approximately 9–10 pairs.

*Dormancy*.—Plants are evergreen and require no dormant period. If grown in appropriate conditions, plants are capable of growing year-round.

Inflorescence:

*Borne*.—Flowers are borne in succession with new buds opening daily atop a tall 3- to 4-branched scape. Scapes may produce approximately 28–35 buds with each branch having 3–7 buds.

*Shape*.—Tall, alternately-branched scape.

*Buds*.—Dimensions: Approximately 8.5 cm to 9.5 cm long and 3.0 cm wide. Color: Basically green, becoming yellower than, but closest to, RHS 168C.

*Individual flowers*.—Number of sepals: three. Number of petals: three. Dimension: The diameter of the flower is approximately 9.0 cm to 10 cm. The sepals are approximately 7.2 cm long and approximately 2.3 cm wide. The petals are approximately 7.2 cm long and approximately 3.9 cm wide. Shape: Funnel-form to campanulate, segments moderately reflexed with age. Petals and sepals slightly wavy along the margins. Color: Upper surface: Petals are orange, RHS 169B; eye zone is more muted than, but closest to, RHS 45A; throat is RHS 151A becoming yellow, RHS 21B, tinged with green. The sepals have a color pattern similar to the petals, however the eye zone colors are less pronounced. Petal mid-vein is RHS 170C–170D. The sepal mid-veins are similar in color but less distinct. Lower surface: Petals and sepals are RHS 169C–D; eye zone is a faintly-apparent, dark band; throat is RHS 151A becoming yellow, RHS 21B, tinged with green. Texture: Moderately thick; leathery. Quantity: Approximately 28–35 flowers/buds present depending on the size of the plant and inflorescence. Branch spikes contain approximately 3 to 7 flowers/buds.

*Senescent flower*.—Spent flowers collapse and shrivel, becoming inconspicuous, eventually falling from the scape in 1 or 2 days.

*Scape*.—Approximately 82 cm to 100 cm in height and 8 mm in diameter measured at the midpoint, RHS 146A.

*Bracts*.—Small leaf-like bracts are present at the junctions of the branches and the scape and of the flower buds and the scape. The bracts are approximately 6.5 cm in length and 3.0 cm in width, RHS 137B–C.

*Time of blooming*.—In mature plants, flowering begins approximately early in the spring (mid-March in Sebring, Fla.).

*Duration of blooms*.—Individual flowers last 1 day, and the total duration of flowering is about 90 days with subsequent scapes appearing throughout the season.

*Fragrance*.—Slight.

Reproductive organs:

*Ovary*.—Superior, oblong, 7 mm long and 4 mm wide, RHS 146D.

*Pistil*.—9.1 cm long and 1.5 mm wide, RHS 23B.

*Stamens*.—Six present; filament is 4.2 cm long and 2 mm wide, RHS 21A.

*Anthers*.—6 mm long, black to brown in color.

*Pollen*.—RHS 23A.

Seed characteristics:

*Seed capsule*.—Oblong, three chambers, 2.9 cm long and 2.2 cm wide, RHS 137B–C.

*Fertility*.—Capable of producing viable seeds and pollen.

Roots: Very thick, fleshy white roots with fine laterals.

Cultural:

*USDA Zone*.—Grows and blooms best when grown in USDA Zones 6 to 11.

Disease/pests: No unusual susceptibilities. Aphids may infest plants during winter months.

I claim:

1. A new and distinct cultivar of Hemerocallis plant named 'Tiger Time' as illustrated and described.

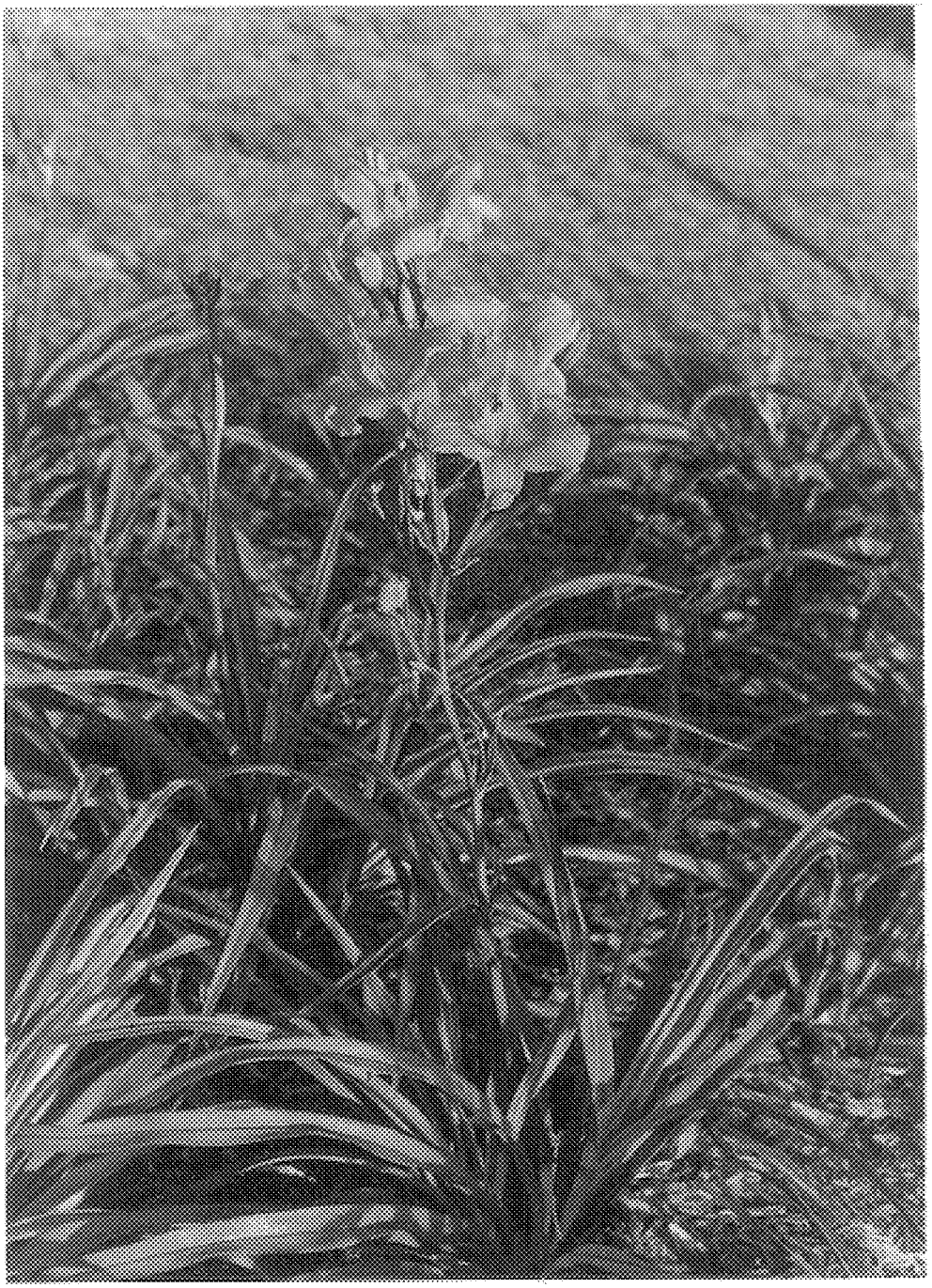

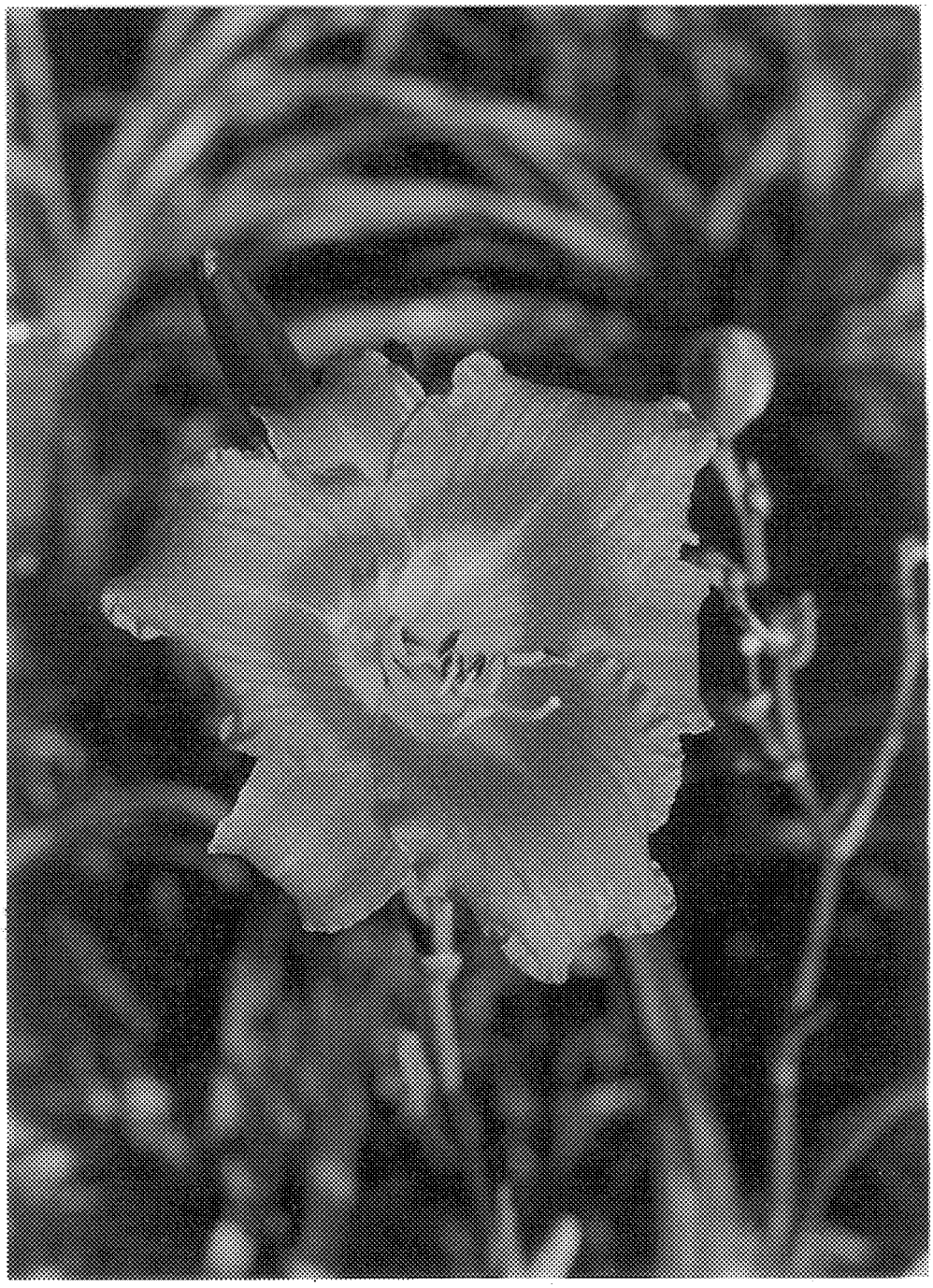

* * * * *